US009149520B2

(12) United States Patent
Walker

(10) Patent No.: US 9,149,520 B2
(45) Date of Patent: Oct. 6, 2015

(54) SAPONIN ADJUVANT COMPOSITIONS AND METHODS RELATING THERETO

(75) Inventor: John Walker, Balwyn (AU)

(73) Assignee: Zoetis Services LLC, Florham Park, NJ (US)

( * ) Notice: Subject to any disclaimer, the term of this patent is extended or adjusted under 35 U.S.C. 154(b) by 0 days.

(21) Appl. No.: 13/420,082

(22) Filed: Mar. 14, 2012

(65) Prior Publication Data

US 2012/0251566 A1 Oct. 4, 2012

Related U.S. Application Data

(63) Continuation of application No. 09/857,797, filed as application No. PCT/AU99/01167 on Dec. 24, 1999.

(30) Foreign Application Priority Data

Jan. 8, 1999 (AU) ........................ PP8073

(51) Int. Cl.
A61K 39/395 (2006.01)
A61K 39/39 (2006.01)
A61K 39/00 (2006.01)

(52) U.S. Cl.
CPC ............ *A61K 39/39* (2013.01); *A61K 39/0006* (2013.01); *A61K 2039/55577* (2013.01); *A61K 2039/55583* (2013.01)

(58) Field of Classification Search
None
See application file for complete search history.

(56) References Cited

U.S. PATENT DOCUMENTS

| 3,632,741 | A | 1/1972 | Wittmann et al. |
| 4,691,008 | A | 9/1987 | Uhmann |
| 4,900,549 | A | 2/1990 | De Vries et al. |
| 4,981,684 | A | 1/1991 | Mackenzie et al. |
| 5,109,026 | A | 4/1992 | Hoskinson et al. |
| 5,324,512 | A | 6/1994 | Ladd |
| 5,378,688 | A | 1/1995 | Nett et al. |
| 5,403,586 | A | 4/1995 | Russel-Jones et al. |
| 5,614,487 | A | 3/1997 | Battersby et al. |
| 5,650,398 | A | 7/1997 | Kensil et al. |
| 5,684,145 | A | 11/1997 | Van Der Zee |
| 5,688,506 | A | 11/1997 | Grimes et al. |
| 6,013,770 | A | 1/2000 | Reeves |
| 6,528,058 | B1 | 3/2003 | Edgar et al. |
| 7,534,441 | B2 * | 5/2009 | McNamara ................. 424/193.1 |
| 8,741,303 | B2 * | 6/2014 | McNamara ................. 424/185.1 |

FOREIGN PATENT DOCUMENTS

| EP | 0 156 280 | 2/1990 |
| GB | 02228-262 A | 1/1990 |
| GB | 2 228 262 | 8/1990 |
| WO | WO 8807574 | 10/1988 |
| WO | WO 9104052 | 4/1991 |
| WO | WO 96/11711 | 4/1996 |
| WO | WO 97/15316 | 5/1997 |
| WO | WO 98/06848 | 2/1998 |
| WO | WO 88/05308 | 7/1998 |
| WO | WO 99/02180 | 1/1999 |
| WO | WO 9927959 | 6/1999 |

OTHER PUBLICATIONS

Ulker, H. et al.; Small Ruminant Research; vol. 45 pp. 273-278 (2002).
Earl, Elizabeth R., et al.; Vaccine; vol. 24 pp. 3172-3183 (2006).
Prendiville, et al.; J. Anim. Sci.; vol. 73 pp. 3030-3037 (1995).
Finnerty, et al., J. Reproduction and Fertility; vol. 101 pp. 333-343 (1994).
Abaza, et al.; J. of Protein Chemistry; vol. 11, No. 5, pp. 433-444 (1992).
Bowers, et al.; Endocrinology; vol. 106 No. 3, pp. 674-683 (1980).
Kaistha, et al.; Indian J. Pathiol Microbiol; vol. 39, No. 4, pp. 287-292 (1996).
Kuby, et al.; Immunology, Second Edition; pp. 86-96 (1994).
Ngo, et al.; The Protein Folding Problem and Tertiary Structure Predictions; pp. 492-495 (1994).
Singh, et al.; Biochem Int.; vol. 25 No. 3, pp. 509-520 (1991).
Talwar, et al.; Int. J. Immunopharmacol; vol. 14, No. 3, pp. 511-514 (1992).
J. A. Turkstra, et al.; Anim. Reproduction Sci.; pp. 247-259.
R. J. Parkinson, et al.; Urology; vol. 45 pp. 171-175 (2004).
T. A. E. Stout, et al.; Anim. Reproduction Sci.; vol. 82-83, pp. 633-643 (2004).
C.A. Herbert, et al.; Anim. Reproduction Sci.; vol. 88, pp. 141-153 (2005).
M. Bonneau, et al.; J. Animal Sci.; vol. 72, pp. 14-20 (1994).
R. E. Flavo, et al.; J. Animal Sci.; vol. 63, pp. 986-994 (1986).
G. Hagen, et al.; Proc. 11th Congress on Animal Production; Abstract 493 (1988).
A. Ladd, et al.; Amer. J. Reproductive Immunology; vol. 22, pp. 56-63 (1990).
S. Sad, et al.; Immunology; vol. 74, pp. 223-227 (1991).
Meloen, et al.; Vaccine; vol. 12, pp. 741-746 (1994).
C. A. Awonyi, et al.; Andrology; vol. 9, pp. 160-171 (1988).
A. Van der Zee, et al.; Vaccine; vol. 13, pp. 753-758 (1995).
R. M. Hoskinson, et al.; Australian J. of Biotechnology; vol. 4 pp. 166-170 (1990).
I. S. Robertson, et al.; Vet. Record; vol. 111, pp. 529-531 (1982).
I. A. Jeffcoate, et al.; Theriogenology; vol. 18, pp. 65-77 (1982).
A. Caraty, et al.; C.R. Acad. Sci. Paris; 303 Series III No. 16, pp. 673-683 (1986).

(Continued)

Primary Examiner — Yunsoo Kim
(74) Attorney, Agent, or Firm — Vyacheslav Vasilyev

(57) ABSTRACT

An adjuvant composition which comprises an anionic macromolecule component particularly an ionic polysaccharide such as DEAE-dextran, and a saponin component, particularly an immunostimulating complex component. Immunogenic compositions comprising an immunogen and this adjuvant composition are also disclosed together with methods of use thereof.

7 Claims, No Drawings

(56) References Cited

OTHER PUBLICATIONS

F. R., Dunshea, et al.; J. Anim. Sci.; vol. 79, pp. 2524-2535 (2001).
X. Y. Zeng, et al.; Anim. Reproduction Sci.; vol. 70, pp. 223-233 (2002).
G. Killian, et al.; Amer. J. of Reproductive Immunology; vol. 55, pp. 378-384 (2006).
Cox, J.C. and Coulter, A.R., "Advances in Adjuvant Technology and Application", in *Animal Parasite Control Utilizing Biotechnolgy*, Chapter 4, Ed. Young, W.K., CRC Press (1992).
Aguado, T. et al. Vaccine 17: 2321-2328 (1999).
Azuma, I. Vaccine 10: 1000-1006 (1992).
Beh, K. and Lascelles, A. K. Immunol. 54: 487-495 (1985).
Dalsgaard, K., Arch. Gesamte Virusforsch. 44 243 (1974).
Fraser, H. M. Immunization with Hormones in Reproductive Research: 107-116 (1975).
Gupta, R. Advanced Drug Delivery Reviews 32: 155-172 (1998).
Hibma M. and Griffin, J. Vet Immunol Immunopath. 31: 279-287 (1992).
Houston, W. E. et al. Infect. and Immun. 13: 1559-1562 (1976).
Potter, A. A. and Manns, J. G., International Patent Application No. PCT/CA97/00559 (1997) (W098/06848).
Wittman et al. Arch. Virol. 47: 225-235 (1975).
Chen, K. S. et al., Canadian Journal of Comparative Medicine, vol. 49, pp. 91-94 (1985).
Carlsson, U. et al., Vaccine, vol. 9, pp. 577-580 (1991).
Kamstrup, S. et al., Vaccine. vol. 17, 1057-1064 (1999).

* cited by examiner ent application is a continuation of U.S. application Ser. No. 09/857,797, filed Sep. 13, 2001, which represents the U.S. National Stage of international application PCT/AU99/01167, filed Dec. 24, 1999. Pursuant to 35 USC section 119, the benefit of Australian priority application PP8073 filed Jan. 8, 1999, is also claimed. The complete disclosure of the '797 parent application is incorporated by reference herein, as if fully set forth.

SEQUENCE LISTING

```
<160> NUMBER OF SEQ ID NOS: 4

<210> SEQ ID NO 1
<211> LENGTH: 10
<212> TYPE: PRT
<213> ORGANISM: Homo sapiens

<400> SEQUENCE: 1

Glu His Trp Ser Tyr Gly Leu Arg Pro Gly
 1               5                  10

<210> SEQ ID NO 2
<211> LENGTH: 10
<212> TYPE: PRT
<213> ORGANISM: Homo sapiens
<220> FEATURE:
<221> NAME/KEY: MOD_RES
<222> LOCATION: (1)
<223> OTHER INFORMATION: Pyro Glu

<400> SEQUENCE: 2

Glu His Trp Ser Tyr Gly Leu Arg Pro Gly
 1               5                  10

<210> SEQ ID NO 3
<211> LENGTH: 8
<212> TYPE: PRT
<213> ORGANISM: Homo sapiens

<400> SEQUENCE: 3

Trp Ser Tyr Gly Leu Arg Pro Gly
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      derivative of listed sequence number 2

<400> SEQUENCE: 4

Gly Ser Gly Ser Gly Leu Arg Pro Gly
 1               5
```

SAPONIN ADJUVANT COMPOSITIONS AND METHODS RELATING THERETO

The present application is a continuation of U.S. application Ser. No. 09/857,797, filed Sep. 13, 2001, which represents the U.S. National Stage of international application PCT/AU99/01167, filed Dec. 24, 1999. Pursuant to 35 USC section 119, the benefit of Australian priority application PP8073 filed Jan. 8, 1999, is also claimed. The complete disclosure of the '797 parent application is incorporated by reference herein, as if fully set forth.

FIELD OF THE INVENTION

The present invention relates generally to an adjuvant composition having high adjuvant properties and low reactogenicity. The adjuvant composition of the present invention is useful where the development of reactogenicity following administration of an immunogenic composition is unacceptable, for example, but not limited to, administration of an LHRH composition as a prophylactic and/or therapeutic agent for the modification of fertility and behaviour patterns of domestic pets or livestock destined for consumption.

BACKGROUND OF THE INVENTION

Bibliographic details of the publications referred to by author in this specification are collected at the end of the description.

Adjuvants are included or added to vaccines and other immunogenic formulations, to increase and in some cases direct the immune response (see reviews by Gupta, 1998, Cox and Coulter, 1992, Azuma, 1992 and Aguado et al, 1999). It will be appreciated that some adjuvants, for example the oil in water and water in oil emulsions, are widely considered as strong adjuvants as they stimulate high levels of antibody, but the reactogenicity of such adjuvants precludes their routine use in many animal species or in man. The unacceptable reactogenicity has been demonstrated in many animals with the traditional Freunds' oil in water emulsion, to the extent that the use of this adjuvant in animals has been prohibited or discouraged in some countries, even for experimental purposes. The use of a combined oil in water/DEAE-dextran adjuvant in cattle (Hodgkinson et al, 1990) resulted in significant and undesirable reactions in 30% of the vaccinated animals.

The most widely used adjuvants in man and animals are based on insoluble aluminium salts, particularly the hydroxide and phosphate forms, commonly and collectively termed "alum". The recent review by Aguado et al (1999) highlights the ongoing need for stronger adjuvants in both man and animals for the development of more effective vaccines.

For example, with a wide range of soluble antigens, the immune response to such an antigen delivered alone is very poor, and in many cases is undetectable even after two vaccinations. Such antigens require the use of an adjuvant to stimulate a consistent immune response. It will be appreciated that known adjuvants offer a range of abilities to stimulate an immune response, most usually defined in terms of antibody response to the immunising antigen.

For haptens coupled to a carrier protein, it is widely recognised that a powerful adjuvant is required. For example, the hypothalmic peptide hormone LHRH is a 10 amino acid peptide that by itself is non-immunogenic. Coupling of LHRH to carrier proteins, for example diphtheria toxoid or ovalbumin provides the necessary T-cell help for an immune response to the LHRH hapten. For other large molecular weight and complex antigens, the T cell help is usually provided by T-cell epitopes within the molecule itself.

The use of DEAE-dextran as an adjuvant has been well described in the scientific literature. Wittman et al (1975), used DEAE-dextran to adjuvant a Foot and Mouth Virus (FMDV) vaccine in pigs, and showed that it induced very high levels of immunity. Houston et al (1976) used this adjuvant at a dose rate of 1-5 mg/kg body weight, to vaccinate monkeys with an equine virus and showed that it induced high titres of antibody. Beh and Lascelles (1985) have also used this adjuvant to immunise sheep with ovalbumin, and showed that it induced higher antibody titres than other soluble adjuvants. None of these studies considered the site reactivity of DEAE-dextran, but they did describe the significant adjuvant effects of DEAE-dextran in these animal species. DEAE-dextran has been used in deer with keyhole limpet haemocyanin (KLH) antigen (Hibma and Griffin, 1992). In this study, DEAE-dextran induced greater IgG responses to KLH than did Freunds adjuvant or alum.

The adjuvant properties of saponin have been long known, as has its ability to increase antibody titres to immunogens. As used herein, the term "saponin" refers to a group of surface-active glycosides of plant origin composed of a hydrophilic region (usually several sugar chains) in association with a hydrophobic region of either steroid or triterpenoid structure. Although saponin is available from a number of diverse sources, saponins with useful adjuvant activity have been derived from the South American tree *Quillaja saponaria* (Molina). Saponin from this source was used to isolate a "homogeneous" fraction denoted "Quil A" (Dalsgaard, 1974).

Dose-site reactivity is a major concern for both the veterinary and human use of Quil A in vaccine preparations. One way to avoid this toxicity of Quil A is the use of immunostimulating complexes (known as Iscoms™, an abbreviation for Immuno Stimulating COMplexes). This is primarily because Quil A is less reactive when incorporated into immunostimulating complexes, because its association with cholesterol in the complex reduces its ability to bind to cholesterol in cell membranes and hence its cell lytic effects. In addition, a lesser amount of Quil A is required to generate a similar level of adjuvant effect.

The immunomodulatory properties of the Quil A saponins and the additional benefits to be derived from these saponins when they are incorporated into an immunostimulating complex have been described in various publications, e.g. Cox and Coulter, 1992; Dalsgaard, 1974; Morein et al., Australian Patent Specifications Nos. 558258, 589915, 590904 and 632067.

Vaccination against the hypothalamic hormone luteinising hormone releasing hormone (referred to herein as "LHRH", also known as GnRH) has been demonstrated as an immunological method of controlling reproduction since the early 1970's (Fraser 1975, Jeffcoate et al 1982). Eliciting an immune response to LHRH prevents the release from the anterior pituitary of the hormones LH and FSH, which are required for the development and maintenance of the gonads—the testes in the male and ovaries in the female. Thus reduction of LH and FSH levels leads to loss of reproductive function.

De-sexing (or neutering) operations are the most widely practised surgical procedures in veterinary medicine and livestock animal management. A significant proportion of both sexes of domestic livestock and companion animals are routinely surgically de-sexed to prevent a variety of undesirable characteristics which accompany sexual maturity. The traits include fighting, wandering, sexual behaviour, loss of condition, tumours of reproductive organs and pregnancy.

The control of mating behaviour by vaccination with LHRH-conjugate vaccines in companion animals such as dogs, cats and horses, and in livestock specifically in male pigs and male and female cattle, has been identified as a goal as significant as the control of fertility.

Similarly, the control and treatment of disorders of the gonads and other reproductive organs, of both humans and animals, such as testicular cancer, breast cancer, prostate cancer, ovarian cancer, prostate enlargement or endometriosis is of significance.

International Patent Application No. PCT/AU98/00532, the contents of which are incorporated herein by reference, discloses that the efficacy of vaccination against LHRH is significantly improved when LHRH is administered as a conjugate with diphtheria toxoid and an ionic polysaccharide such as DEAE-dextran. However, although the efficacy is improved, this formulation nevertheless induces reactogenicity such as visible swelling, that may be long-lasting, at the site of administration. In some instances, such as where the formulation is used to vaccinate domestic pets (for example, dogs) or livestock destined for consumption the occurrence of such reactogenicity following vaccination against LHRH utilising this formulation is unacceptable. Accordingly, there is a need to develop a LHRH vaccine which exhibits both efficacy and low reactogenicity.

In one aspect of the work leading up to the present invention, it has been determined that reactogenicity of LHRH conjugated to diphtheria toxoid and an ionic polysaccharide can be reduced when a proportion of the ionic polysaccharide component is replaced with a saponin component, particularly an immunostimulating complex.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Sequence Identity Numbers (SEQ ID NOS.) for the nucleotide and amino acid sequences referred to in the specification are defined following the bibliography. A summary of the SEQ ID NOS. is provided after the Examples.

One aspect of the present invention relates to an adjuvant composition which comprises an ionic macromolecule component and a saponin component, particularly an immunostimulating complex component.

Such an adjuvant composition has been found to have high adjuvant activity combined with low reactogenicity. The advantage of this combined adjuvant over other known adjuvants is that it possesses an unusual combination of properties including:
a) an ability to elicit a very strong immune response to a range of antigens and
b) to have at the same time very low reactogenicity or reactivity,
c) the reactogenicity is lower than that of the more reactogenic component in the combination, and
d) the adjuvant effect or immunostimulating effect is greater than that of either of the component adjuvants alone.

In yet another aspect there is provided an adjuvant composition which comprises an ionic polysaccharide component and a saponin component, particularly an immunostimulating complex component.

In still yet another aspect there is provided an adjuvant composition which comprises an ionic polysaccharide component and a saponin component, particularly a protein-free immunostimulating complex component.

In a further aspect of the present invention there is provided an immunogenic composition comprising an immunogen and an adjuvant composition, which adjuvant composition comprises an ionic macromolecule component and a saponin component, particularly an immunostimulating complex component.

In another further aspect there is provided an immunogenic composition comprising an immunogen and an adjuvant composition, which adjuvant composition comprises an ionic polysaccharide component and a saponin component, particularly an immunostimulating complex component.

In still another further aspect there is provided an immunogenic composition comprising an immunogen and an adjuvant composition, which adjuvant composition comprises an ionic polysaccharide component and a saponin component, particularly a protein-free immunostimulating complex component.

In still another further aspect of the present invention there is provided a pharmaceutical composition comprising an immunogenic composition as broadly described above, together with one or more pharmaceutically acceptable carriers and/or diluents.

Another aspect of the present invention relates to a method of eliciting, in an animal, an effective immune response, said method comprising administering to said animal an effective amount of an immunogenic composition as broadly described above.

In yet another aspect, the present invention provides the use of an adjuvant composition as broadly described above in the manufacture of a composition for eliciting an effective immune response in an animal.

DETAILED DESCRIPTION OF THE INVENTION

The present invention is predicated, in part, on the determination that when the ionic polysaccharide component of the vaccine comprising LHRH conjugated to diphtheria toxoid as disclosed in International Patent Application No. PCT/AU98/00532 is combined with an immunostimulating complex, the reactogenicity of the immunogenic composition is reduced without significant reduction in efficacy.

Accordingly, one preferred aspect of the present invention relates to an immunogenic composition for use in eliciting an effective immune response to LHRH, said composition comprising a LHRH-diphtheria toxoid conjugate and an adjuvant composition, which adjuvant composition comprises an ionic polysaccharide or other ionic macromolecule component and a saponin component, particularly an immunostimulating complex component.

The development of reactogenicity to an immunogenic preparation, such as at the site of administration of a vaccine, is usually assessed by reference to the development of a number of symptoms including symptoms of inflammation such as swelling which is detectable either by palpation or, if more severe, by the eye, redness, and abscess formation. The degree of reactogenicity is usually determined by reference to the occurrence, duration and severity of any one or more of these symptoms. For example, reactogenicity which results in visible abscess formation is of greater severity than reactogenicity which involves only swelling. Further, swelling which is visible to the eye is a more severe form of reactogenicity than swelling which is detectable only by palpation. In accordance with the present invention, reference to reactogenicity which is "low" should be understood as reactogenicity which produces either no detectable symptoms or symptoms which are not visible to the eye. For example, swelling which is detectable only by palpation is an example of reactogenicity which is low. The present invention should be understood to extend to the complete absence of any reactogenicity. In the context of the present invention, low reactogenicity may also be taken to include visible swelling of only short duration.

Reference to an "ionic macromolecule" or an "ionic polysaccharide" should be understood as a reference to any positively or negatively charged polysaccharide or other macromolecule, or derivative or chemical equivalent thereof. Reference to "derivative" and "chemical equivalent" should be understood to have the same meaning as outlined below.

The polysaccharide or other macromolecule may be chemically modified to introduce charged groups, so that it becomes highly charged. In solid form or when in solution, the charged groups are paired with a counter ion so that the overall net charge is zero or close to zero. The polysaccharide may be selected from any one of a number of such molecules, preferably soluble molecules to aid in sterilisation for example by filtration, but the polysaccharide is not restricted to soluble polysaccharides, as insoluble materials may be sterilised by irradiation, wet or dry heat or other processes that do not rely on solubility. Preferably the polysaccharide is a polymer of glucose, linked alpha 1-6 to form a soluble dextran, although insoluble forms of dextran linked alpha 1-3 may also be used.

The polysacharide or other macromolecule may be modified to give strong positive (+ve) charged groups at pH values between 5.0 and 8.0. The modifying group can be selected from any one of a number of +ve charged groups, but preferably is a diethyl-aminoethyl (DEAE) group. An alternative +ve charged polysaccharide is QAE-dextran. The modified dextran known as DEAE-dextran, may have a molecular size in the range 50,000 Da to $5 \times 10^6$ Da, preferably a molecular weight range of 500,000 to $1.5 \times 10^6$ da. It is known that such large macromolecules as dextran are heterogeneous in size, typically with 95% of the material within approximately a 4 fold size range. The level of modification is high, such that on average every third glucose residue is substituted with a DEAE group. Such material may be purchased commercially or manufactured from dextran. Alternatively, the dextran or other polysaccharide may be negatively charged, for example by modification with sulphate groups. Preferably, the ionic polysaccharide component of the adjuvant composition of the present invention is a DEAE-dextran component.

The saponin component may, for example, be Quil A or another purified or semi-purified saponin preparation (including a mixture of saponin fractions). Preferably, the saponin component is provided in the form of an immunostimulating complex.

Immunostimulating complexes (or Iscom™) which are incorporated in the adjuvant composition in accordance with the present invention may be prepared by techniques which are well known to persons skilled in the art, and which are described in detail in the publications of Cox and Coulter, 1992 and Morein et al., Australian Patent Specifications No. 558258, 589915, 590904 and 632067 the disclosures of which are incorporated herein by reference.

Briefly, immunostimulating complexes are typically, but not limited to, small cage like structures 30-40 nM in diameter. The final formulation of an immunostimulating complex with an optimal amount of protein is a molar ratio of Quil A, cholesterol, phosphatidyl choline and protein in a ratio of 5:1:1:1. An immunostimulating complex may contain, for example, 5 to 10% by weight Quil A, 1 to 5% cholesterol and phospholipids and the remainder protein. Peptides can be incorporated into the immunostimulating complex either directly or by chemical coupling to a carrier protein (e.g. diphtheria toxoid or influenza envelope protein) after incorporation of protein into immunostimulating complexes. Reference to an "immunostimulating complex" should be understood to include reference to derivatives, chemical equivalents and analogues thereof. For example, reference to a derivative of an immunostimulating complex includes reference to an immunostimulating complex in which one or more of Quil A, cholesterol, phosphatidyl choline or protein, for example, are deleted or where a component in addition to Quil A, cholesterol, phosphatidyl choline or protein is added to the complex. The functional equivalent of an immunostimulating complex may be an immunostimulating complex in which one or more of its four components are replaced with a functional equivalent. In a preferred embodiment of the present invention, the protein component of the immunostimulating complex is deleted. This type of immunostimulating complex is herein referred to as a "protein-free immunostimulating complex" (or Iscomatrix™).

The immunostimulating complex in the adjuvant composition of the present invention should be oppositely charged to the ionic polysaccharide component. Thus in the preferred combination with positively charged DEAE-dextran, the immunostimulating complex is negatively charged. This desirable characteristic may be achieved by incorporation of charged saponins into the structure. Formation of an effective adjuvant composition by combining an immunostimulating complex with negatively charged polysaccharide component would require that the immunostimulating complex be positively charged. In an alternate form, a positively charged immunostimulating complex would be combined with a negatively charged ionic-polysaccharide component.

A wide range of antigens, or other immunogens may be combined with the novel adjuvant composition of the present invention, including soluble protein antigens, peptide hapten conjugated to a carrier protein and whole virus as antigen. In addition, prior knowledge of adjuvants and their activity, other antigens such as recombinant proteins, antigenic polysaccharides, antigenic lipids, peptides and other particulate antigens may also be suitably used with this adjuvant composition.

The final formulation is to be used to raise an immune response against the antigen of choice. Both immunostimulating complexes loaded with antigen or protein-free immunostimulating complexes may be used to form the adjuvant composition. The combination adjuvant may be formed with antigen first incorporated into the immunostimulating complex. In an alternate form, antigen may be added to the combination adjuvant after formulation of the adjuvant. This has many advantages in manufacture of vaccines, both experimentally and commercially, as the one form of adjuvant may be used for a wide range of antigens.

DEAE-dextran is known in the art to be a very strong adjuvant, but often with unacceptable reactogenicity. Immunostimulating complexes are known to be acceptable adjuvants on their own, but with a far lesser degree of immunostimulating activity when compared to DEAE-dextran. More specifically, the new adjuvant is a carefully controlled combination of DEAE-dextran and immunostimulating complex, the controlled ratio being that which maintains the adjuvant activity of both components, particularly of the more powerful adjuvant DEAE-dextran but also of immunostimulating complexes, but the combination is such that the unwanted reactogencicity of the DEAE-dextran is neutralised. In the art, it is expected that combinations of adjuvants will be more reactogenic than the individual components. Such is the case with DEAE-dextran combined with oil emulsions (Hodgkinson et al, 1990).

Extensive experimentation in a range of animal species has shown that the mass ratio of ionic polysaccharide such as DEAE-dextran over that of immunostimulating complex may be critical to obtaining a combination adjuvant of low reactogenicity. Reducing the level of DEAE-dextran by 10 fold would result in a combination adjuvant of weak activity, but also low reactogenicity. As demonstrated in the Examples, using a higher level of DEAE-dextran with a lower ratio of immunostimulating complexes, e.g. a mass ratio of 208, results in a combination adjuvant of slightly lower immunostimulating activity, but unacceptably higher reactogenicity.

The mass ratios referred to herein relate to the preferred adjuvant composition comprising DEAE-dextran in which the dextran is substituted about every third glucose residue, and a protein-free immunostimulating complex having a Quil A:cholesterol: phospholipid ratio of 5:1:1.

Formulations with a mass ratio in the range of 50 to 300 have been found to be effective, with a preferred range of 100 to 140. A preferred formulation is one with a mass ratio of DEAE-dextran to immunostimulating complex of 125. This is exemplified by vaccines containing about 10 mg DEAE-dextran and about 80 µg immunostimulating complex for use in smaller or more sensitive animals such as dogs or man, or similarly about 100 mg DEAE-dextran with about 800 µg immunostimulating complex, or about 150 mg DEAE-dextran with about 500 µg immunostimulating complex, for use in larger animals such as horses, cattle, sheep and pigs.

Reference to an "effective" immune response should be understood as a reference to an immune response which either directly or indirectly leads to a desired prophylactic or therapeutic effect. In the case where the immunogen comprises a LHRH-diphtheria toxin conjugate, such a response includes the reduction or complete blocking of reproductive function (i.e. reduces or prevents the development of or functioning of any one or more of the reproductive organ's activities or modulates the hormonal levels of an animal such that any one or more aspects of reproduction or reproductive activity are reduced) in at least 90%, and preferably at least 95%, of animals treated. It should be understood that efficacy is a functional measure and is not defined by reference to anti-LHRH antibody titre alone since the presence of circulating antibody alone is not necessarily indicative of the capacity of said circulating antibody to block reproductive function. The term "reproductive organ" should be understood in its broadest sense to refer to the male and female gonads and accessory sexual organs. "Accessory sexual organs" should also be understood in its broadest sense and includes, for example, the prostate, breasts, seminal vesicles and the uterus.

Reference hereinafter to "LHRH" should be read as including reference to all forms of LHRH and derivatives, equivalents and analogues thereof.

Reference to "derivatives, equivalents and analogues" should be understood to include reference to fragments, parts, portions, chemical equivalents, mutants, homologues and analogues from natural, synthetic or recombinant sources, including fusion proteins. For example, with respect to LHRH, said LHRH includes peptides comprising a sequence of amino acids substantially as set forth in SEQ ID NO:1 or SEQ ID NO:2 or SEQ ID NO:3 or SEQ ID NO:4 or having at least 50% similarity thereto. The molecules defined in SEQ ID Nos:1, 2 and 3 are from the human and are conserved across all mammals. SEQ ID NO:4 is a derivative of SEQ ID NO:2 wherein spacers have been introduced at the N-terminus. Chemical equivalents of LHRH can act as a functional analogue of LHRH. Chemical equivalents may not necessarily be derived from LHRH but may share certain similarities. Alternatively, chemical equivalents may be specifically designed to mimic certain physiochemical properties of LHRH. Chemical equivalents may be chemically synthesised or may be detected following, for example, natural product screening.

Homologues of LHRH contemplated herein include, but are not limited to, LHRH derived from different phyla including birds, fish, reptiles and invertebrates.

"Derivatives" may also be derived from insertion, deletion or substitution of amino acids. Amino acid insertional derivatives include amino and/or carboxylic terminal fusions as well as intrasequence insertions of single or multiple amino acids. Insertional amino acids sequence variants are those in which one or more amino acid or non-natural amino acid residues are introduced into a predetermined site in the protein although random insertion is also possible with suitable screening of the resulting product. Deletional variants are characterised by the removal of one or more amino acids from sequence. Substitutional amino acid variants are those in which at least one residue in the sequence has been removed and a different natural or non-natural residue inserted in its place. Typical substitutions are those made in accordance with Table 1:

TABLE 1

Suitable residues for amino acid substitutions

| Original Residue | Exemplary Substitutions |
| --- | --- |
| Ala | Ser |
| * Arg | Lys |
| Asn | Gln; His |
| Asp | Glu |
| Cys | Ser |
| Gln | Asn |
| * Glu | Ala |
| * Gly | Pro |
| * His | Asn; Gln |
| Ile | Leu; Val |
| * Leu | Ile; Val |
| Lys | Arg; Gln; Glu |
| Met | Leu; Ile |
| Phe | Met; Leu; Tyr |
| * Ser | Thr |
| Thr | Ser |
| * Trp | Tyr |
| * Tyr | Trp; Phe |
| Val | Ile; Leu |

Key:
Amino acid residues marked with an asterisk indicate residues present in the mammalian LHRH sequence.

Examples of non-natural amino acids include, but are not limited to the D-isomers of said amino acids. "Additions" to amino acid sequences include fusion with other peptides, polypeptides or proteins.

Reference to diphtheria toxoid should be understood as a reference to all forms of diphtheria toxoid and derivatives thereof. The term "derivatives" has the same meaning as hereinbefore defined. Derivatives may include, for example, molecules comprising the diphtheria toxoid T cell epitopes or said T cell epitopes in isolation.

Preferably, said LHRH comprises an LHRH C-terminal fragment of at least five amino acids. More preferably, said LHRH is full length LHRH or "LHRH 1-10 form" which comprises the amino acid sequence substantially as set forth in SEQ ID NO:1. Even more preferably, said LHRH comprises the amino acid sequence substantially as set forth in SEQ ID NO:2 and wherein the carboxyl terminus of said amino acid sequence is amidated. Said preferred LHRH is referred to herein as "LHRH 2-10 form".

Accordingly, in one preferred embodiment, there is provided a composition for use in eliciting an effective immune response to LHRH comprising a LHRH 2-10 form-diphtheria toxoid conjugate and an adjuvant composition, which adjuvant composition comprises an ionic polysaccharide component (preferably a DEAE-dextran component) and a saponin component, particularly an immunostimulating complex component.

In another embodiment, there is provided a composition for use in eliciting an effective immune response to LHRH comprising a LHRH 2-10 form-diphtheria toxoid conjugate and to an adjuvant composition, which adjuvant composition comprises an ionic polysaccharide component (preferably a DEAE-dextran component) and a saponin component, particularly a protein-free immunostimulating complex component.

Although not intending to limit this embodiment of the invention to any one method, the LHRH peptide may be synthesised by Fmoc chemistry and the resulting peptide coupled to the carrier protein diphtheria toxoid. Said coupling may be performed as described in Ladd et al 1990 or in Bonneau et al 1994, and the resulting conjugate of peptide and carrier protein (referred to herein as "peptide-conjugate") processed to be free of unbound peptide and other by-products of conjugation. Such processing may be achieved by conventional dialysis or by ultrafiltration. The resulting peptide-conjugate is adsorbed to the ionic polysaccharide adjuvant.

Still without limiting the present invention to any one theory or mode of action, administration of an effective amount of the LHRH preparation of the present invention induces a significantly more effective immune response against LHRH than the LHRH-carrier-adjuvant compositions described in the prior art. Said improved efficacy is observed when the immunogenic LHRH composition specifically comprises the carrier diphtheria-toxoid and an ionic polysaccharide adjuvant. By replacing a portion of the ionic polysaccharide component with an immunostimulating complex component, the reactogenicity of the LHRH-conjugate preparation can be reduced while maintaining its efficacy.

LHRH-conjugate preparations suitable for use in accordance with the present invention preferably comprise 5-500 µg of LHRH-diphtheria toxoid conjugate in 5-500 mg ionic polysaccharide (such as DEAE-dextran)/40-4000 µg immunostimulating complex (such as Iscomatrix™).

Pharmaceutical compositions in accordance with the present invention may be administered by injection by any of the routes currently known in the art of vaccinology, e.g. by subcutaneous, intramuscular, intradermal injection or by oral administration, or by application to mucosal membranes, either by direct application in solution or gel or other suitable formulation, or by aerosol administration to the nasal or respiratory surfaces. Preferably the formulation is administered by subcutaneous or intramuscular injection.

The formulation may be stored as a solid, frozen or dried, either by freeze drying or lyophilisation, or by spray drying or other forms of drying.

The pharmaceutical forms suitable for injectable use include sterile aqueous solutions (where water soluble) or dispersions and sterile powders for the extemporaneous preparation of sterile injectable solutions or dispersion. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or salts such as sodium chloride. Prolonged absorption or delayed release of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying, the freeze-drying technique and the spray-drying technique which yield a powder of the active ingredients plus any additional desired ingredient from previously sterile-filtered solution thereof.

When the active ingredients are suitably protected they may be orally administered, for example, with an inert diluent or with an assimilable edible carrier, or they may be enclosed in hard or soft shell gelatin capsule, or compressed into tablets, or incorporated directly with the food of the diet. For oral administration, the active compound may be incorporated with excipients and used in the form of ingestible tablets, buccal tablets, troches, capsules, elixirs, suspensions, syrups, wafers, and the like. The percentage of the compositions and preparations may, of course, be varied and may conveniently be between about 5 to about 80% of the weight of the unit. The amount of active compound in such useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; and a lubricant such as magnesium stearate. When the dosage unit form is a capsule, it may contain, in addition to materials of the above type, a liquid carrier. Various other materials may be present as coatings or to otherwise modify the physical form of the dosage unit. A syrup or elixir may contain the active compound, methyl and propylparabens as preservatives, and a dye. Of course, any material used in preparing any dosage unit form should be veterinarily pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for veterinarily active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. For administration to livestock it is particularly advantageous to use a multi-dose container linked to a repeating vaccination gun. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 µg. Expressed in proportions, the active compound is generally present in from about 0.5 µg to about 2000 µg/ml of carrier. In the case of compositions containing supplementary active ingredients, the dosages are determined by reference to the usual dose and manner of administration of the said ingredients.

Reference to "animal" should be understood as the reference to all animals including primates (e.g. humans, monkeys), livestock animals (e.g. sheep, cows, horses, donkeys, goats, pigs), laboratory test animals (e.g. rats, guinea pigs, rabbits, hamsters), companion animals (e.g. dogs, cats), captive wild animals (e.g. emus, kangaroos, deer, foxes), ayes (e.g. chickens, ducks, bantams, pheasants, emus, ostriches), reptiles (e.g. lizards, snakes, frogs) and fish (e.g. trout, salmon, tuna). Said animal may be male or female.

Further features of the present invention are more fully described in the following Examples. It is to be understood, however, that this detailed description is included solely for the purposes of exemplifying the present invention. It should not be understood in any way as a restriction on the broad description of the invention as set out above.

Example 1

Preparation of LHRH-Conjugate Preparation

The LHRH-conjugate is based on a synthetic 2-10 form of Luteinising Hormone Releasing Hormone (LHRH) peptide coupled to a carrier protein. The peptide by itself is too small to be antigenic, and coupling to a carrier protein is required so that the peptide acts as a hapten and immunity is induced to LHRH. The carrier protein is diphtheria-toxoid.

The peptide is synthesised by Fmoc chemistry and the resulting 2-10 form LHRH peptide is coupled to diphtheria toxoid. The coupling may be performed as described in Ladd et al. 1990 or in Bonneau et al. 1994, and the resulting conjugate of peptide and diphtheria-toxoid processed to be free of unbound peptide and other by-products of conjugation. Such processing may be achieved by conventional dialysis or by ultrafiltration.

The resulting LHRH-carrier protein preparation may be used to prepare a composition for administration by formulation with or in an adjuvant. The levels of active component and adjuvant are in part dependent on the species being targeted and are chosen to achieve the desired level and duration of the immune response required and on the lack of reactogenicity (ie tissue compatibility).

Example 2

A. Preparation of Protein-Free Immunostimulating Complex (Iscomatrix™)

Quil A (Superfos, Denmark) solution (sterile) and dipalmitoyl phosphatidyl choline (DPPC)/cholesterol solution in 20% Mega 10 detergent are aseptically combined under GMP conditions in a sterile temperature controlled reaction vessel in quantities calculated to result in starting proportions of 5:1:1 for Quil A:DPPC:cholesterol (by weight). After reaction, the preparation is ultrafiltered to remove unincorporated starting materials and free Mega 10 detergent. This preparation, known as Iscomatrix™, is essentially a preformed adjuvant consisting of protein-free immunostimulating complex particles.

B. Preparation of Combination Adjuvant Comprising DEAE-Dextran and Iscomatrix™

DEAE-dextran (Pharmacia, MW range 500,000 to 1,500, 000) is simply prepared as a 20% w/v solution by first dissolution in water, the pH adjusted to 7.5 with NaOH, the volume adjusted to give the required concentration and then sterilised by filtration.

Iscomatrix™ and DEAE-dextran plus antigen are then mixed in the appropriate ratios, followed by the addition of diluent to adjust the final volume to achieve the correct concentration of all of the components of the vaccine.

An appropriate volume of DEAE-dextran is first added to a sterile mixing vessel containing a suitable stirring device. For volumes less than 2 liters, a magnetic stirring bar is suitable. The appropriate volume of Iscomatrix™ (~2 mg/mL) is then added, followed by the appropriate volumes of antigen and then diluent to bring the material to the correct volume. The diluent of choice is of low ionic strength, to bring the whole final formulation to approximate isotonicity and thus avoid pain on injection due to hyper-tonicity or higher than physiological osmolarity. This is of particular importance in the art of vaccine formulation, as severe pain resulting from injection is highly undesirable and would render the whole formulation unsuitable. The diluent found to be suitable for a canine vaccine is sterile water for injection, ie pyrogen free distilled water.

Example 3

A. Preparation of Vaccines for Dog Trials a. DEAE-Dextran Adjuvant Alone.

The formulation required to be tested in this trial was a 1 mL dose containing 50 mg DEAE-dextran, 200 µg LHRH-diphtheria toxoid conjugate, with thiomersal (0.01%) added as preservative, in sterile phosphate buffered saline.

The adjuvant for this vaccine is prepared by dissolving DEAE-dextran in distilled water and adjusting the pH to 7.5 with sodium hydroxide. The final concentration of the DEAE-dextran is adjusted to 20% w/v by the addition of distilled water, after pH adjustment. The solution is then sterile filtered. LHRH peptide (2-10 LHRH) is conjugated to diphtheria toxoid as described in Example 1. The conjugate preparation is sterile filtered and the protein concentration determined by standard methods, e.g. the BCA protein assay. The preparation used for this study was 5.7 mg protein/mL.

b. Iscomatrix™ Adjuvant Alone.

The formulation required to be tested in this trial was a 1 mL dose containing 60 µg Iscomatrix™, 200 µg LHRH-diphtheria toxoid conjugate, with thiomersal (0.01%) added as preservative in sterile phosphate buffered saline.

The adjuvant for this vaccine, Iscomatrix™, is prepared as described in Example 2A using Quil A as the saponin derivative, together with cholesterol, dipalmitoyl phosphatidyl choline (DPPC) and Mega 10 as the detergent. The process is performed under sterile conditions with all components sterilised prior to addition. The Quil A concentration was determined to be 2.24 mg/ml.

LHRH peptide (2-10 LHRH) is conjugated to diphtheria toxoid as described in Example 1. The conjugate preparation is sterile filtered and the protein concentration determined by standard methods, e.g. the BCA protein assay. The preparation used for this study was 5.7 mg protein/mL.

c. Iscomatrix™ DEAE-Dextran

The formulation required to be tested in this trial was a 1 mL dose containing 60 µg Iscomatrix™+10 mg DEAE-dextran, 200 µg LHRH-diphtheria toxoid conjugate, with thiomersal (0.01%) added as preservative, in sterile phosphate buffered saline.

The adjuvant for this vaccine is a compound adjuvant, obtained by combining appropriate proportions of Iscomatrix™ and DEAE-dextran. Iscomatrix™, is prepared as described in Example 2A. DEAE-dextran is prepared as described in above.

LHRH peptide (2-10 LHRH) is conjugated to diphtheria toxoid as described in Example 1. The conjugate preparation is sterile filtered and the protein concentration determined by standard methods, e.g. the BCA protein assay. The preparation used for this study was 4.9 mg protein/mL.

B. Vaccination of Dogs

All trials were conducted in an identical manner.

Dogs of 6-12 months of age and of mixed sex were housed in indoor pens with free access to outdoor runs. They were fed a commercially available balanced diet.

Dogs (groups of 7) were vaccinated subcutaneously in the scruff of the neck at 0 and 4 weeks with a 1 mL dose of vaccine. All vaccines were administered from a 2 mL syringe fitted with a 23 gauge needle.

Dogs were bled at regular intervals to monitor antibody levels to LHRH. Reactogenicity of the vaccines was determined by close examination of the dogs after vaccination.

Examination was by visual inspection and by thorough manual palpation of the vaccine site and surrounding area.

Site reactions were scored by close visual examination and physical palpation of the injection site and surrounding area. Reactions were scored as:
0 No visible or detectable reaction
1 Reaction only detectable by palpation
2 Visible reaction detectable without palpation
3 Severe abscessed reaction Site Reaction Scores

| Vaccine Formulation | 1 Week PB | | | 2 Weeks PB | | | 4 Weeks PB | | |
|---|---|---|---|---|---|---|---|---|---|
| | 0 | 1 | 2 | 0 | 1 | 2 | 0 | 1 | 2 |
| DEAE-dextran (50 mg) | 3/7 | 2/7 | 2/7 | 3/7 | 4/7 | — | 7/7 | — | — |
| Iscomatrix ™ (60 μg) | 7/7 | — | — | 7/7 | — | — | 7/7 | — | — |
| DEAE-dextran (10 mg) + Iscomatrix ™ (60 μg) | 5/7 | 1/7 | 1/7 | 7/7 | — | — | 7/7 | — | — |

(Note: PB = post-boost)

These results show that the DEAE-dextran formulation is much more reactive than either the Iscomatrix™ formulation or the Iscomatrix™+DEAE-dextran formulation. With DEAE-dextran alone, significant reactions (Score 1 or greater) persisted for at least 2 weeks. With the Iscomatrix™ formulation, reactions were not detected and with the DEAE-dextran+Iscomatrix™ formulation, minor reactions in 2/7 dogs persisted for only 1 week.

In order to provide a more quantitative indication of reactogenicity, the approximate volumes of the site reactions, when detected, were measured as width×length×height, in cm. The results for 1 and 2 week post-boost (PB) from the above table are given below. Site reaction volumes are not given for the Iscomatrix™ vaccine formulation group, as no site reactions were detected.

Site Reaction Volumes

| Vaccine Formulation | Week 1 PB Site Reaction Volumes (cm³) | | | Week 2 PB Site Reaction Volumes (cm³) | | |
|---|---|---|---|---|---|---|
| | Score 0 | 1 | 2 | Score 0 | 1 | 2 |
| DEAE-dextran (50 mg) | — | 32, 4 | 40, 8 | — | 6.25, 1 0.5, 0.5 | — |
| Iscomatrix ™ (60 μg) + DEAE-dextran (10 mg) | 1.1 | 6 | — | — | — | — |

These results show that the degree of reactogenicity is much less in the Iscomatrix™+DEAE-dextran formulation than with the DEAE-dextran formulation alone as shown by the size of the reactions.

Example 4

Vaccination of Dogs with Varying Ratios of DEAE-Dextran and Iscomatrix

Beagle foxhound cross dogs (groups of 8 or 13) were vaccinated with formulations of 2-10 LHRH linked to DT. The active component was formulated in either DEAE-dextran alone, Iscomatrix alone or in the combination adjuvant DEAE-dextran plus Iscomatrix.

A) DEAE-dextran vaccines: Each dose was contained in a volume of 1 mL formulated to contain either 10 mg or 50 mg of DEAE-dextran with 200 μg 2-10 LHRH-DT conjugate.
B) Iscomatrix: Each dose was formulated in 1 mL with either 60 μg or 150 μg Iscomatrix with 200 μg 2-10 LHRH-DT conjugate.
C) Combination adjuvant: Each dose was contained in a volume of 1 mL formulated to contain DEAE-dextran and Iscomatrix in the ratios indicated below with 200 μg 2-10 LHRH-DT conjugate.

The combination adjuvant contained either:
1. 10 mg DEAE-dextran with 60 μg Iscomatrix—referred to as 10/60 vaccine
2. 12.5 mg DEAE-dextran with 60 μg Iscom™atrix—referred to as 12.5/60 vaccine
3. 10 mg DEAE-dextran with 80 μg Iscomatrix—referred to as 10/80 vaccine Vaccination Schedule:

These formulations were administered to dogs by subcutaneous injection at 0 and 4 weeks. Blood samples were taken at 2 weeks after the second vaccination and assayed for antibodies to LHRH.

Site reactions were determined by careful palpation of the injection site and surrounding tissue at weekly intervals. The site reaction data presented are at post boost (PB) vaccination. Reaction to vaccination may in certain circumstances be increased with continuing vaccination, and thus the reactogenicity post boost may be considered as more stringent test than post primary vaccination.

Site Reaction Scores

Site reactions are scored by close inspection and palpation, with the score on the following scale:
0 No visible or detectable reaction.
1 Reaction only detectable by palpation
2 Visible reaction detectable without palpation
3 Severe abscessed reaction

| Vaccine Formulation | 1 Week PB | | | 2 Weeks PB | | | 4 Weeks PB | | |
|---|---|---|---|---|---|---|---|---|---|
| | 0 | 1 | 2 | 0 | 1 | 2 | 0 | 1 | 2 |
| DEAE-dextran (10 mg) | 1/8 | 2/8 | 4/8 | 4/8 | 2/8 | 1/8 | 7/8 | 0/8 | 0/8 |
| DEAE-dextran + Iscomatrix ™ 12.5/60 Vaccine | 5/8 | 1/8 | 2/8 | 5/8 | 1/8 | 2/8 | 7/8 | 1/8 | 0/8 |
| DEAE-dextran + Iscomatrix ™ 10/80 Vaccine | 11/13 | 2/13 | 0/13 | 10/13 | 3/13 | 0/13 | 12/13 | 1/13 | 0/13 |

Site Reaction Volumes

Volumes are calculated from the measured size of the local reaction determined by palpation, and are volumes are expressed in mL. This measure gives a better indication of the severity of the site reactions.

| Vaccine Formulation | 1 Week PB | | | 2 Weeks PB | | | 4 Weeks PB | | |
|---|---|---|---|---|---|---|---|---|---|
| | 0 | 1 | 2 | 0 | 1 | 2 | 0 | 1 | 2 |
| DEAE-dextran (10 mg) | — | 0.12, 5, 0.75 | 24, 12, 9, 3 | — | 0.25 | 1.7 | — | — | — |
| DEAE-dextran + Iscomatrix ™ 12.5/60 Vaccine | — | — | 32, 2 | 0 | 1.5 | 1.8, 3 | — | 0.03 | — |
| DEAE-dextran + Iscomatrix ™ 10/80 Vaccine | — | 0.25 | — | 0 | 0.06, 0.5, 2 | — | — | — | — |

Summary:

These data in dogs with 2-10 LHRH diphtheria toxoid conjugate show that combination adjuvants with varying ratios of DEAE-dextran to Iscomatrix have varying degrees of reactogenicity. Comparison of the site reactogenicity of the various formulations indicates that, compared to dextran, the combined adjuvant formulated at a ratio of 12.5 mg DEAE-dextran to 60 µg Iscomatrix is as reactogenic if not more reactogenic than the same dose of DEAE-dextran alone. This is a mass ratio of 208.

In contrast, the formulation containing 10 mg DEAE-dextran to 80 µg Iscomatrix has significantly less reactivity than either DEAE-dextran alone or the 12.5/60 formulation. This formulation did not give visible reactions at any time after injection, and comparison of reaction volumes indicates that at all times after injection, the 10/80 formulation far fewer reactions and those few that do occur, with a peak of 3 of 13 dogs at 2 weeks post more acceptable and of shorter duration. This has a mass ratio of 125.

The immunostimulatory effectiveness of an adjuvant may be judged by the magnitude and duration of the antibody response elicited. The antibody titres at 8 weeks post boost are shown below for the DEAE-dextran and combination adjuvants.

Antibody titres to LHRH (8 Weeks Post-Boost)

| Vaccine Formulation | Geometric mean titre | Range |
|---|---|---|
| Iscomatrix (150 µg/dose) | 12244 | 3761-58097 |
| Iscomatrix ™ (60 µg/dose) | 3965 | 3322-7343 |
| DEAE-dextran (50 mg/dose) | 38913 | 23166-50377 |
| DEAE-dextran (10 mg/dose) | 6917 | 2007-24477 |
| DEAE-dextran + Iscomatrix ™ 10/60 Vaccine | 11686 | 4149-35112 |
| DEAE-dextran + Iscomatrix ™ 12.5/60 Vaccine | 9670 | 4191-54737 |
| DEAE-dextran + Iscomatrix ™ 10/80 Vaccine | 19456 | 9730-50644 |

Summary:

The titres in the above table show that the 10/80 vaccine (mass ratio 125) is a stronger immunostimulant than either the combination adjuvant 12.5/60 vaccine (mass ratio 208) or 10 mg DEAE-dextran sole adjuvant vaccine.

Of particular note is the effectiveness of the 10/80 vaccine in raising the minimum titre of the lowest responder dogs. Vaccine efficacy is in many instances reduced by the ineffective response in a small proportion of the test population and is not usually determined by a maximal and effective response in proportion of the test population.

Both of the combined adjuvant vaccines are more effective than the DEAE-dextran alone formulation or the Iscomatrix based vaccine. The response of the combination adjuvant is greater than the additive effect and thus the two components may be judged to be acting in synergy. The mass ratio of 125 is more effective in increasing the lower responding dogs.

Example 5

Vaccination of Sheep with Bovine Viral Diarrhoea Virus (BVDV) in Combination Adjuvant 1. Growth and Inactivation of Bovine Viral Diarrhoea Virus (BVDV): Growth of Viral Antigen:

Two strains of BVDV virus were used, Trangie and Bega, isolated from infected cattle in Australia. The growth medium used was Eagles minimum essential medium containing non essential amino acids single strength and 3% bicarbonate, 2% HEPES and 2% adult bovine serum.

A 1×1700 $cm^2$ roller bottle was inoculated with Trangie (AJ050) at a multiplicity of infection (MOI) of 0.1. The bottle was incubated with rolling for 5 days at 37° C., then frozen. A 1×1700 $cm^2$ roller bottle inoculated with Bega (WVS p3) at a MOI of 1.0 and was incubated with rolling for 5 days at 37° C., then frozen. Roller bottles were thawed and the antigen content tested by antigen specific ELISA assays. The characteristics of the preparations used in the vaccine formulation are as follows:
  Trangie: E2 (surface glycoprotein) level=⅛
    NS3 (non structural protein) level=⅛
  Bega: E2 level=⅛
    NS3 level=¼
Inactivation:
50 mls of each virus was dispensed into a 500 ml bottle
Add 50 mls/liter of 2.8% sodium bicarbonate=5 mls
Add 20 mls/liter of 1M HEPES buffer=2.1 mls
Add 1 ml/liter of 13 propriolactone (BPL)=107 μl Contents were transferred to a new 500 ml bottle containing a magnetic stirrer and stirred at 2-8° C. for 21 hours. Inactivated material was transferred to 37° C. and stirred for another 3 hours to hydrolyse any remaining BPL.

2. Vaccine Formulation:

Combination adjuvant: Each dose comprised 2 mls of inactivated virus and 1 ml of combination adjuvant.

The bulk vaccine was formulated as:

30 mls inactivated Bega and Trangie 15 mls of combination adjuvant, (111 mg DEAE-dextran and 880 μg Iscomatrix/mL, Equal to a mass ratio of 125)

450 μl thiomersal as preservative.

Iscom™ adjuvant: Each dose comprised both strains of virus and 2 mg Iscom™ as Quil A equivalent, in a total volume of 2 mL.

The vaccines were dispensed into a bulk plastic pillow pack after being mixed by vortexing and inversion and stored at 2-8° C.

Vaccination Schedule:

Both vaccines were administered as indicated below:

Day 0: Sheep were with either 3 mls each of combination adjuvant vaccineor 2 mls of Iscom™ vaccine, administered subcutaneously in the neck.

Day 28: Each animal given a second dose of vaccine administered as above.

Groups: 10 sheep were vaccinated with the Iscom™ adjuvanted vaccine.

4 sheep were vaccinated with the combination adjuvant vaccine.

Site Reactions:

Combination adjuvant: Sheep were examined at 7 day intervals after the primary and secondary vaccination. One of the 4 sheep developed a score 1 site reaction (small swelling palpable, not visible) after the primary vaccination. This was resolved by 2 weeks post vaccination.

Iscom™: Sheep were examined at 6 days after boost. 7 of 10 sheep had large reactions at the site of injection.

Summary: The combination adjuvant had smaller and less frequent site reactions, indicating that it induced lower levels of reactogenicity.

Example 6

Vaccination of Mice with Ovalbumin in Combination Adjuvant

C57/Blk6 mice (n=3 per grp) were vaccinated subcutaneously with chicken egg albumin (ovalbumin, OVA) formulated in either:

1. 0.625 mg DEAE-dextran
2. 5 μg Iscomatrix
3. 0.625 mg DEAE-dextran with 5 μg Iscomatrix. This is a vaccine containing the preferred combined adjuvant of mass ratio formulation of 125.

Each dose of the above vaccines contained 12.5 μg ovalbumin in a 100 μL volume, the volume and concentration of the components being adjusted with sterile water for injection.

The mice were vaccinated only once subcutaneously and blood samples taken 14 days later after the primary vaccination at euthanasia. Sera so obtained were assayed for IgM and IgG responses to OVA.

Mice were monitored for health and signs of systemic reactogenicity.

Reactogenicity:

Mice in the DEAE-dextran and combination adjuvant groups remained well for the 14 days after primary vaccination.

However, 2 of the 3 mice vaccinated with Iscomatrix died with 8 days of vaccination. Toxicity of Iscoms™, saponins and Iscomatrix to mice is well known. The mice in the combination adjuvant group remained well, indicating that the combination adjuvant is less reactogenic systemically.

Antibody Titres:

Sera obtained 14 days after the primary immunisations were assayed for IgG and IgM antibody titres to ovalbumin by ELISA assay.

Mouse IgM Titres to Ovalbumin, 14 Days Post Primary Vaccination.

All titres shown are as ELISA optical density at 1/200 serum dilution.

| | Vaccine formulation | | | | | | |
|---|---|---|---|---|---|---|---|
| | DEAE dextran | DEAE dextran | DEAE dextran | Iscomatrix ™ | Comb. Adj. | Comb. Adj. | Comb. Adj. |
| OD at 1/200 | 0.581 | 0.895 | 0.487 | 0.275 | 0.778 | 0.571 | 0.414 |

Mouse IgG Titres to Ovalbumin, 14 Days Post Primary Vaccination

All titres shown are as ELISA optical density at 1/200 serum dilution.

| | Vaccine formulation | | | | | | |
|---|---|---|---|---|---|---|---|
| | DEAE dextran | DEAE dextran | DEAE dextran | Iscomatrix ™ | Comb. Adj. | Comb. Adj. | Comb. Adj. |
| OD at 1/200 | 0.753 | 0.771 | 0.745 | 0.493 | 0.495 | 0.618 | 0.716 |

Summary:

The data above shows that immunisation of mice with the soluble antigen OVA in all of the adjuvants tested induced an antibody responses in both the IgM and IgG isotypes 14 days after a single vaccination.

The combination adjuvant and DEAE-dextran alone formulation elicited higher antibody responses than the Iscomatrix adjuvanted vaccine.

To those skilled in the art, it would be expected that a single vaccination of mice with a soluble antigen in the presence of an adjuvant would give rise predominantly to an IgM response.

The combined adjuvant induced a strong IgG response in mice vaccinated with OVA 14 days after a single vaccination. This result supports the previous published conclusion (Houston et al, 1976) that DEAE-dextran adjuvant shortens the period to switching from an early IgM to IgG response and thereby increases the IgG response to vaccination at an early stage. This also seems to be a property of the combination adjuvant.

Example 7

Vaccination of Cattle with 2-10 LHRH-DT in Combination Adjuvant

Vaccines and Vaccination Schedule:

Heifers (female cattle) were administered by subcutaneous injection, vaccines formulated with 200 µg 2-10 LHRH conjugate and either:
1. DEAE-dextran (200 mg/dose)—50 heifers
2. Combination adjuvant (150 mg DEAE-dextran with 500 µg Iscomatrix, Mass ratio 300)—6 heifers.

All vaccines were formulated as a 2 mL dose.

Vaccines were given at week 0 and week 4, with a 2 week post boost bleed being taken at week 6.

Site reactions were scored at 2 weeks post boost on a semi-quantitative scale from 0 to 3.

Blood samples were taken by venepuncture of the jugular or tail vein at 2 weeks post boost (week 6). Sera were obtained from the blood samples by allowing them to clot and separation by centrifugation. Serum titres of the IgG isotype were assayed to LHRH by ELISA.

Site Reactions.

Site reaction scores, scored on a scale of:
0 No visible or detectable reaction.
1 Reaction only detectable by palpation
2 Visible reaction dectable without palpation
3 Severe abscessed reaction

| Vaccine Formulation | 2 Weeks PB Score | | | |
|---|---|---|---|---|
| | 0 | 1 | 2 | 3 |
| DEAE-dextran 50 heifers | 32 | 7 | 8 | 3 |
| DEAE-dextran + Iscomatrix ™ 6 heifers | 1 | 1 | 4 | 0 |

Summary:

The use of DEAE-dextran as adjuvant resulted in severe site reactions of score 3 (abscess) in 3 of the vaccinated cattle.

The combination adjuvant did not induce severe reactions in any of the cattle, with no score 3 lesions occurring.

Antibody Titres:

Serum IgG titres to LHRH at 2 weeks post boost vaccination were determined by ELISA.

| Vaccine Group | Group mean titre | Range of titres |
|---|---|---|
| DEAE-dextran | 4181 | 100-16836 |
| DEAE-dextran + Iscomatrix ™ | 15869 | 1841-51920 |

Summary:

The combination adjuvant induced high tires in all vaccinated cattle with a group mean titre of over 15,000. By comparison, the use of DEAE-dextran alone as adjuvant resulted in a lower group mean titre of 4181, with a much lower range of responses.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Aguado, T. et al. *Vaccine* 17:2321-2328 (1999).
Awonyi, C. A., Chandrashekar, V., Arthur, R. D., Schanbacher, B. D. and Falvo, R. E. J. *Androl.* 9:160-171 (1988).
Azuma, I. *Vaccine* 10:1000-1006 (1992).
Beh, K. and Lascelles, A. K. *Immunol.* 54:487-495 (1985).
Bonneau, M., Dufour, R., Chouvet, C., Roulet, C., Meadus, W. and Squires, E. J. *J. Animal Science* 72: 14-20 (1994).
Caraty, A. and Bonneau, M. C. R. *Acad. Sci. Paris* 303 Series D:673-683 (1986).
Cox, J. C. and Coulter, A. R., "Advances in Adjuvant Technology and Application", in *Animal Parasite Control Utilizing Biotechnology*, Chapter 4, Ed. Yong, W. K., CRC Press (1992).
Dalsgaard, K., *Arch. Gesamte Virusforsch.* 44:243.
Falvo, R. E., Chandrashekar, V. et al. *J. Animal Science* 63: 986-994 (1986).
Fraser, H. M. *Immunization with Hormones in Reproductive Research:* 07-116 (1975).
Gupta, R. *Advanced Drug Delivery Reviews* 32:155-172 (1998).
Hagen, G., Andresen, O., Blichfeldt, T. and Berg, K. A. *Proc. 11th Congress on Animal Production Abstract* 493 (1988).
Hibma M. and Griffin, *J. Vet. Immunol. Immunopath.* 31:279-287 (1992).
Hodgkinson, R. M. et al. *Aust. J. Biotechnology* 4:166-170 (1990).
Hoskinson, R. M., Rigby, P. E., Mattner, V. L., Huynh, V. L., D'Occhio, M. D., Neish, A., Trigg, T. E., Moss, B. A., Lindsey, M. J., Coleman, G. D. and Schwartzkoff, C. L. *Aust. J. Biotechnol.* 4:166-170 (1990),
Houston, W. E. et al. *Infect. and Immun.* 13:1559-1562 (1976).
Jeffcoate, I. A., Lucas, J. M. and Crighton, D. B. *Theriogenology* 18:65-77 (1982).
Ladd A., Tsong Y. Y., and Thau R. B., *American J. Reproductive Immunology* 22: 56-63 (1990).
Meloen, et al., *Vaccine* 12: 741-746 (1994).
Potter, A. A. and Manns, J. G., International Patent Application No. PCT/CA97/00559 (1997).
Robertson, I. S., Fraser, H. M., Innes, G. M. and Jones, A. S. *Vet. Record* 111:529-531 (1982).
Sad S., Gupta H., Talwar G. P., and Raghupathy R., *Immunology* 74:223-227 (1991).
Wittman et al. *Arch. Virol.* 47:225-235 (1975).
Zee, A., Noordegraaf, C. V., Bosch, H., Gielen, J., Bergmans, H., Hoekstra, W. and Die, I. *Vaccine* 13:753-758 (1995).

The invention claimed is:

1. A method of eliciting an effective immune response in an animal against LHRH, comprising administering to an animal an effective amount of a liquid vaccine composition that comprises:
   (1) an LHRH-diphtheria toxoid conjugate;
   (2) an adjuvant that comprises (a) an ionic polysaccharide, and (b) immunostimulating complexes that comprise a saponin, a sterol, and a phospholipid; and
   (3) optionally, a pharmaceutically acceptable carrier.

2. A method of eliciting an effective immune response in an animal, comprising administering to an animal an effective amount of a single dose of the vaccine composition of claim 1.

3. The method of claim 1 wherein the adjuvant provides a mass ratio of ionic polysaccharide to immunostimulating complex in the range of about 100 to about 140.

4. The method of claim 1, wherein the immunostimulating complex is a protein-free immunostimulating complex.

5. The method of claim 1, wherein the ionic polysaccharide is DEAE-dextran or QAE-dextran.

6. The method of claim 1, wherein the vaccine composition provides from about 5 to about 500 µg of LHRH-diphtheria toxoid conjugate, from about 5 to about 500 mg of the ionic polysaccharide, and from about 40 to about 4000 µg of the immunostimulating complex.

7. A method of eliciting an effective immune response in an animal, comprising administering to an animal an effective amount of two or more doses of the vaccine composition of claim 1.

* * * * *